United States Patent [19]

Schmitt

[11] Patent Number: 5,266,471
[45] Date of Patent: Nov. 30, 1993

[54] SOLID CARRIERS MODIFIED WITH 2,4,6-TRICHLORO-S TRIAZINE TO IMMOBILIZE BIOMOLECULES

[75] Inventor: Stefan Schmitt, Heidelberg, Fed. Rep. of Germany

[73] Assignee: ROHM, Darmstadt, Fed. Rep. of Germany

[21] Appl. No.: 660,052

[22] Filed: Feb. 25, 1991

[30] Foreign Application Priority Data

Feb. 25, 1990 [DE] Fed. Rep. of Germany ....... 4005927

[51] Int. Cl.$^5$ ............... C12N 11/10; C12N 11/08; G01N 33/544; G01N 33/545; G07K 17/00
[52] U.S. Cl. .................. 435/178; 435/179; 435/180; 435/181; 436/529; 436/530; 436/531; 436/532; 525/327.6; 530/813; 530/814; 530/815; 530/816
[58] Field of Search ............... 435/177, 178, 179, 180, 435/181; 525/327.6; 436/529, 530, 531, 532; 530/813, 814, 815, 816

[56] References Cited

U.S. PATENT DOCUMENTS

| | | | |
|---|---|---|---|
| 3,674,767 | 7/1972 | Lilly et al. | 435/178 X |
| 3,824,150 | 7/1974 | Lilly et al. | 195/63 |
| 4,179,337 | 12/1979 | Davis et al. | 530/303 X |
| 4,190,713 | 2/1980 | Kraemer et al. | 435/180 X |
| 4,229,537 | 10/1980 | Hodgins et al. | 435/178 X |
| 4,357,311 | 11/1982 | Schutt | 424/12 |
| 4,511,694 | 4/1985 | Kramer et al. | 526/210 X |

FOREIGN PATENT DOCUMENTS

| | | |
|---|---|---|
| 1212058 | of 0000 | Canada . |
| 0260098 | 3/1988 | European Pat. Off. . |
| 2722751 C3 | 9/1982 | Fed. Rep. of Germany . |
| 1585628 | 1/1970 | France . |
| 2212500 | 7/1989 | United Kingdom . |
| 2221466 | 2/1990 | United Kingdom . |

OTHER PUBLICATIONS

Nature, vol. 216, Nov. 4, 1967, pp. 514–515, G. Kay, et al. "Coupling of Enzymes to Cellulose Using Chloro-S-Triazines".

*Primary Examiner*—David M. Naff
*Attorney, Agent, or Firm*—Oblon, Spivak, McClelland, Maier & Neustadt

[57] ABSTRACT

A modified solid carrier is used to covalently immobilize biomolecules such as proteins. The carrier is based on well-known matrix materials modified to have covalently bound functional groups of formula I

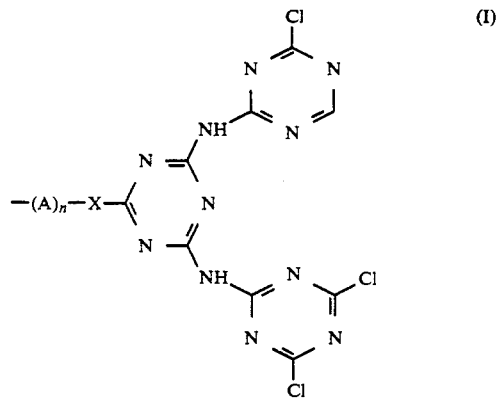

that are suitable for covalent immobilization, where A is a spacer group; X is O, S, or NH and n is 0 or 1. The modified solid carrier is prepared by reacting ammonia with glycidyl groups of a carrier to form α-hydroxy-β-amino groups, reacting these groups with 2,4,6-trichloro-s-triazine to form an N-triazinyl group-containing carrier, reacting this carrier with ammonia and reacting the resultant carrier with 2,4,6-trichloro-s-triazine.

18 Claims, No Drawings

SOLID CARRIERS MODIFIED WITH 2,4,6-TRICHLORO-S TRIAZINE TO IMMOBILIZE BIOMOLECULES

BACKGROUND OF THE INVENTION

1. Field of the Invention

The invention relates to modified, solid carriers to immobilize biomolecules, e.g. proteins, and a process to bind proteins.

2. Discussion of the Background

The immobilization of biologically significant proteins on carriers represents an excellent instrument both in biochemical research and in biotechnology (cf. Ullmann's Encyclopedia of Industrial Chemistry, 5th ed., vol. A14, pp. 2–42, VCH 1989).

To date, suitable solid organic matrix materials have been primarily (modified) polysaccharides, proteins and active carbon from natural sources, synthetic polymers such as polystyrene, poly(meth)acrylates, polyacrylamides, maleic anhydride polymers, vinyl and allyl polymers and polyamides. Suitable inorganic carriers are minerals, in particular clay materials, diatomaceous earth and talcum as well as synthetic materials such as glass, metal oxides and metals. Of the possible types of fixation to the matrix, covalent bonding is preferred for the activity determining structures of the biologically active substances that are to be fixed into position. The active substances are predominantly proteins. The carrier materials themselves usually do not have any reactive groups in order to link them to the active groups of the proteins (especially amino, hydroxyl or phenol, amide, thiol, carboxyl groups), but rather they require activation. To activate the carrier materials a range of reactive groups have been introduced. For example, groups that produce an alkylation or acylation of free amino, phenol and/or thiol groups of the biologically active proteins (cf. Ullmann's Encyclopedia, loc. cit., U.S. Pat. No. 4,829,101; CA-A 1,212,058). This group includes, e.g., the polymer-bonded chloro-s-triazinyl group, which, primarily bonded to cellulose, serves to directly couple the proteins (cf. B. P. Surinev et al., Biokhimiya, 31, 387 (1966); G. Kay et al., Nature, 216 (1967), 514; Biochim. Biophys. Acta, 198, (1970), 276).

A carrier system that is commercially available is the cross-linked copolymer comprising acrylamide or methacrylamide and glycidyl acrylate or glycidyl methacrylate and/or allyl glycidyl ether, which is made preferably of bead-shaped particles. Such matrix polymers are specified in the DE-C 27 22 751, U.S. Pat. No. 4,190,713 and U.S. Pat. No. 4,511,694. The epoxy functions of such a carrier system can be condensed directly with nucleophilic groups on the protein surface, however, they can also be linked as bifunctional reagents by means of dicarboxylic acid bishydrazides. (GB-A 2,212,500). Of significant practical interest are also membrane matrix materials as carriers of biologically active proteins, in particular immunologically relevant proteins or enzymes.

SUMMARY OF THE INVENTION

One object of the present invention is to improve the application properties of the solid carrier materials, in particular of the aforementioned types. Thus, the object is not to make available types of carriers that are fundamentally new but rather structures resulting from modification, whose bondability and bonding properties are improved. The object is described in detail with the examples of carrier polymers, synthesized from (meth)acrylamide and glycidyl (meth)acrylates, and membrane matrix polymers.

DETAILED DESCRIPTION OF THE PREFERRED EMBODIMENTS

The above described cross-linked copolymers of (meth)acrylamide and glycidyl (meth)acrylate or allyl glycidyl ether have proven to be valuable carrier systems for different isolation and purification operations in biochemistry. (Cf. E.L.V. Harris and S. Angal in Protein Purification Methods, pp. 261–269, I.R.L. Press, 1989).

The excellent application properties of this carrier make it desirable to further improve its efficiency by modifying this carrier structure and others in general. For example, it is desirable to increase the bonding rates of biologically effective proteins to the carrier system, if possible without having to accept other drawbacks such as reduced stability or greater sensitivity under reaction conditions.

It has now been found that this problem can be solved in an excellent manner by the solid carriers modified according to invention. The invention relates to modified solid carriers, which contain at least an adequate number of functional groups of formula I in order to fix biologically active substances, in particular proteins,

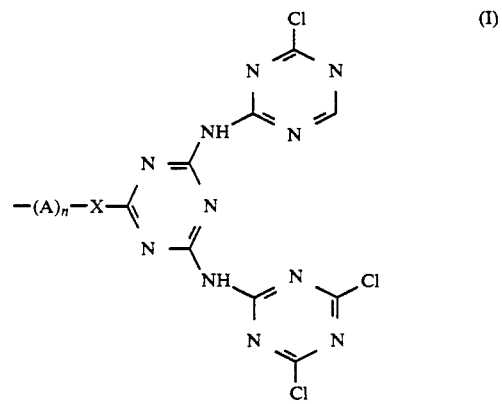

wherein A stands for a spacer group; X for O,S or —NH and n for 0 or 1, connected by covalent bonding to the carrier material. When A is contained as a spacer group in (I), it denotes an alkylene or an arylene group containing at least two members and up to six members and which can itself be a component of the solid carrier or can be subsequently linked to the solid carrier. This linking can be done, e.g. through alkylation, esterification, amide formation or etherification (cf. H. J. Rehm and G. Reed, Vol. 7a, Enzyme Technology, Chapter 7, pp. 347–384 ff, VCH 1987). Especially preferred is A of the formula

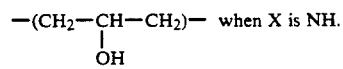

Starting from well-known carrier materials which contain an adequate number of nucleophilically reacting XM groups, where X has the meaning specified above for formula I and M is hydrogen or if X is O or S, X may also be a metal cation, especially an alkali cation, preferably sodium or potassium, the modified solid carriers are generally manufactured with 2,4,6-trichloro-s-triazine (cyanuric chloride) in a reaction comprising at least three stages. The reaction with an adequate quantity of 2,4,6-trichloro-s-triazine, followed by substitution of chlorine groups on the triazine with amino groups and further reaction of the amine-substituted triazine with 2,4,6-trichloro-s-triazine groups produced. The preparation of a preferred embodiment of the modified, solid carrier of the invention is described below.

This especially advantageous embodiment is a process of preparing solid carriers containing functional groups, by starting from a carrier material which has a number of glycidyl groups of formula II

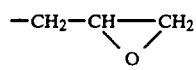
(II)

as the functional groups. In the first step, the carrier material is reacted with ammonia, transforming the glycidyl groups of formula II into α-hydroxy-β-amino groups of formula III $$-CH_2-\overset{OH}{\underset{|}{CH}}-CH_2NH_2.$$ (III)

In a second step the α-hydroxy-β-amino groups of formula II are converted to N-triazinyl-substituted groups of formula IV with 2,4,6-trichloro-s-triazine, by eliminating the NCl

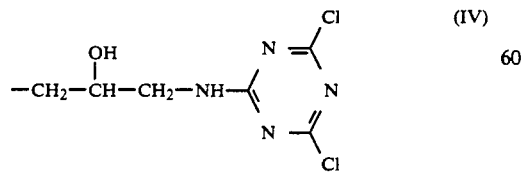
(IV)

which in a third stop are converted through treatment with ammonia into amine-substituted groups of formula V

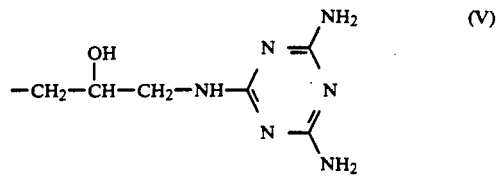
(V)

which, after reaction with at least two equivalents of 2,4,6-trichloro-s-triazines is converted to the groups of formula I.

Especially preferred are modified, solid carriers which are obtained according to the aforementioned process starting with cross-linked copolymers of methacrylamide/acrylamide and glycidyl acrylate/glycidyl methacrylate, preferably in bead form, as the matrix polymer. In so doing, N,N-methylene-bis-methacrylamide is preferably used as the cross-linking monomer.

The structure of these matrix polymers can be shown schematically with the following formula (cf. E. L. V. Harris and S. Angal, loc. cit., pp. 261–262).

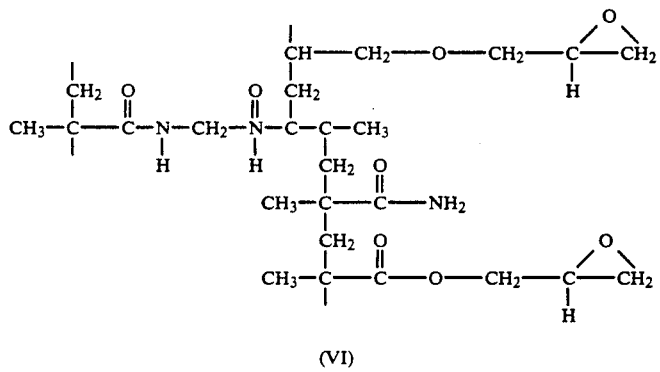
(VI)

Such matrix polymers are described in the DE-C 27 22 751, U.S. Pat. No. 4,190,713 and U.S. Pat. No. 4,511,694. The beads generally have a diameter ranging from 5 to 1,000 μm, in particular 30 to 1,000 μm and exhibit an inner cavity (hollow beads). The content of glycidyl groups in the matrix polymer that can undergo a reaction with ammonia is from about 0.8 to 2.5 μmol per mg of dry carrier material. Other characteristics for a commercially available matrix polymer (EUPERGIT C of Rohm GmbH), which is representative of matrix polymers of this type, can be seen in the following table.

| CHARACTERISTICS | SPECIFICATION |
| --- | --- |
| averge particle size | 140–180 μm |
| pore diameter | 40 nm |
| reject limit = $M_1$ TM | $2 \times 10^5$ Daltons |
| bonding-active surface | 180 m²/g (dry) |
| epoxide content | 800–1,000 μmol/g (dry) |
| water absorption | 2.3 ml/g (dry) |
| density = $d_4^{20}$ | 1.20 |
| bonding capacity (under normal conditions) | 0.34 g/ml |
| human albumin | 48 mg/g (moist) |
| human IgG | 34 mg/g (moist) |
| swelling properties with respect to water | 1:1.4<br>1 ml (dry) yields 1.4 ml (moist) |
| solubility (in water, buffers and organic solvents) | insoluble |

| CHARACTERISTICS | SPECIFICATION |
|---|---|
| pressure stability | 300 bar |

Under the electron microscope one can detect the macroporous structure of the beads which have channels and cavities and a diameter ranging from 0.1 to 2.5 μm (1,000-25,000 Å), i.e. of an order of magnitude that enzyme or substrate molecules having a size of 10-100 Å can reach the entire interior of the macroporous matrix.

Instead of the above specified matrix polymers, those having an average pore size of 30-80 μm, prepared by substantially identical chemical synthesis as described above, can be used. Such products are commercially available under the name EUPERGIT C30N. Moreover, matrix polymers, prepared by similar synthesis, but with a pore size in the range of 200-250 μm are suitable. They are commercially available under the name EUPERGIT C 250 L. Other matrix polymers that can be used exhibit, in principle the same chemical composition as the matrix described above, but are compact, i.e., have no significant pore content. Products with an average particle size ranging from approximately 0.6 to 1.4 μm are commercially available under the name EUPERGIT CIZ. More information about the aforementioned commercial products is available in the chemical literature. Further, systems with adequate surfaces (CA-A 1,212,058) and nuclear shell latices U.S. Pat. No. 4,829,101) can also serve as the starting materials.

As stated above, other types of matrix materials are also suitable as starting materials to prepare modified, solid carriers, especially those having glycidyl groups of formula II in the starting material. These include, e.g., polysaccharides such as cellulose, agarose, sepharose.

The glycidyl(epoxy) groups II can also be introduced, e.g., by means of a reaction with 1,4-bis(2,3-epoxypropoxy)butane into the polysaccharides (cf. Dechema Monographs No. 1724-1731, vol. 84, "Characterization of Immobilized Biocatalysts", Ed. K. Buchholz, Verlag Chemie 1979; P. Vretblad, FEBS Lett., 47 (1974) 86).

Furthermore, as stated above, membranes carrying amino groups are of special interest as carrier materials. Such membranes can simultaneously contain amino groups and carboxyl groups, i.e., be designed so as to be amphoteric. For example, such a membrane matrix material can be a polycondensation product of hexanediamine and adipic acid similar to Nylon 66. Such polymers can be represented by the formula VI

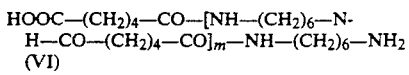

(VI)

where, m ranges from about 80 to 100.

Suitable membrane materials are available, e.g., under the name BIODYNE A (amphoteric nylon 66) of Pall, Bio Support Division, Portsmouth, UK.

The biologically significant proteins which are bound to the solid carriers of the invention have already been characterized above in a general manner. As a rule, they exhibit nucleophilic groups, such as OH, SH and preferably amino groups, which react with the functional groups (see formula I) of the carriers under biologically acceptable conditions. They may be biocatalysts such as enzymes as well as cells, cell organelles and immunologically active materials and structures, in particular antibodies. The immobilized biocatalysts can produce or transform very different kinds of substrates such as amino acids, peptides and enzymes, sugars, organic acids, antibiotics, steroids, nucleosides and nucleotides, lipids, terpenoids and key organic chemicals (cf. Ullmann, 5th edition, vol. 9A, loc. cit, pp. 389-390).

Suitable immunologically active structures are, e.g., microorganisms such as gram positive and gram negative bacterial spirochetes, mycoplasma, mycobacteria, vibrios, actinomycetes, protozoa such as intestinal protozoa, amoeba, flagellates, sporozoa, intestinal nematodes and tissue nematodes (worms), trematodes (schistosomes, leeches), cestodes, toxoplasma, and fungi such as sporotichum, cytocoecus, blastomyces, histoplasma, coccidioides, candida, viruses and rickettsias such as dog hepatitis, Shope papilloma, influenza A and B, fowl plague, herpes simplex, adenovirus, polyane, Rous sarcoma virus, smallpox virus, poliovirus, measles, canine distemper, leukemia, mumps, Newcastle disease, Sendai, ECHO, hoof and mouth disease, psittacosis, rabies, extromelia, tree viruses, tissue antigens, enzymes such as pancreas chymotrypsinogen, procarboxypeptidase, glucose oxidase, lactate dehydrogenase, uricase, amino acid oxidase, urease, asparaginase, proteases, blood cell antigens, blood group substances and other isoantigens such as blood platelets, leukocytes, plasma proteins, and antibodies including auto-antibodies. Preferred are monoclonal antibodies, which are directed against antigens of bacterial or viral origin, against autoimmune antigens and antibodies and against tumor antigens, tissue antigens and others.

Of special interest is, for example, the covalent bonding of "protein A". By "protein A" is meant the known cell wall protein, which is responsible for binding immunoglobulin G (IgG), for example, from Staphylococcus aureus. Its isolation by affinity chromatography and its use as an immunosorbent for isolation of immunoglobulins is known. See Hjelm H. et al, FEBS Lett., 28, 73-76 (1972).

Other examples of proteins to be immobilized are, in particular protein G, protein A/G, trypsin inhibitor, anti-IgG, monoclonal and polyclonal antibodies as well as the enzymes pepsin and papain.

To prepare the modified carrier of the present invention, a solid carrier material that has a number of glycidyl groups of formula II as functional groups, preferably those of formula II as a functional group on EUPERGIT C is introduced in a suitable vessel. To the carrier is added ammonia, e.g. equimolar aqueous ammonia, at room temperature. For example, for 1.0 g of dry matrix material 4 ml of aqueous ammonia are added. Preferably the mixture is allowed to take react for more than 1 day, as a reference point, more than approximately 72 hours, preferably with slight shaking and the gel is washed with distilled water. Treatment with mercaptoethanol to saturate the residual epoxy groups has proven to be an expedient measure. One incubates for a few hours, preferably overnight (approximately 12 hours) while shaking slightly at room temperature. Thereupon the gel is washed with distilled water and dried, for example, on a frit while washing with acetone. The gel can be completely dried in a vacuum drying oven, preferably at 35° to 45° C. To the dried matrix polymer an inert alkaline buffer, e.g., sodium carbonate buffer with a pH of 10.8 ("SC-buffer") is added in quantities of about 10 ml of buffer to 1.0 g of matrix polymer. To this, the 2,4,6-trichloro-s-triazine ("trichloro-triazine"), in a suitable dry inert solvent such as acetone, is added preferably drop-by-drop at room temperature, while stirring gently in such a manner that to 1.0 g of amino-substituted matrix polymer about 0.15 g of trichloro-triazine in approximately 2 ml of solvent are used. After incubation for a few minutes, for example approximately 10 minutes, at room temperature preferably while shaking slightly and the pH is readjusted with 0.1M SC-buffer to pH 10.8. The product is then washed and dried with an inert solvent, for example with 50% aqueous acetone, on a fritted glass column.

To this product is added in a suitable container, 25% aqueous ammonia, preferably in such quantities that for 1.0 g of dry trichloro-triazine-substituted matrix polymer about 10 ml of aqueous ammonia are added. The mixture is incubated for a period of time, for example 30 minutes at elevated temperature (about 55° to 65° C.), preferably at approximately 60° C. while shaking. The product is then washed with water in portions, with preferably a total of 100 ml of water and subsequently with acetone (approximately 5 ml) and the gel that is formed (and whose functional groups correspond to formula V) is sucked dry. To this dried gel 0.1M SC-buffer, for example 10 ml, is added and then trichloro-triazine in acetone is added slowly drop-wise (approximately 2 minutes) so that for 1.0 g of original amino-substituted matrix polymer about 0.3 g of trichloro-triazine, preferably in approximately 2 ml of acetone, are added. After incubation for a short period of time, preferably approximately 8 minutes at room temperature while shaking gently, the pH is adjusted by means of SC-buffer to a pH of 10.8.

The gel that is formed is preferably washed, preferably with 50% (vol.) aqueous acetone, preferably with approximately 100 ml, sucked dry on a frit and freeze dried. The matrix polymer that is obtained in this manner and that is modified with functional groups of formula I can be stored as such in dry storage, with or without cooling, or used directly.

When XM groups as defined above are used, especially amino group-carrying membrane materials, one may proceed as follows. The membrane material is positioned and 2,4,6-trichloro-s-triazine, preferably dissolved in a suitable inert solvent such as nitromethane, is added dropwise. After trichloro-s-triazene addition, one incubates, preferably for a relatively short period of time, i.e., about 10 minutes, at room temperature and while gently shaking. The membrane is washed with a solvent such as nitromethane and dried for example, in air. Ammonia, for example in the form of 25% aqueous ammonia, is added to the dried reaction product and then incubated, preferably at an elevated temperature of about 60° C. and for about ½ hour, preferably while shaking gently. Subsequently, the product is washed with water and dried again. Then, an adequate quantity of 2,4,6-trichloro-s-triazine is added again, preferably dissolved in a solvent, and preferably through slow dropwise addition. One incubates again for a short period of time, for a little more than 8 minutes and at room temperature and while shaking gently. Then one washes with a solvent. The modified carrier material is subsequently air-dried and then freeze-dried.

A first approximation of the content of bondable units of formula I in the final product can be derived from the generally known content of functional groups of formula II in the starting materials. Generally, about 0.25 g of matrix polymer to about 5–10 mg of the protein to be immobilized are used. A suitable buffer, preferably as standard phosphate buffer, i.e., phosphate buffered saline (PBS) in quantities of about half the volume of the carrier gel is preferably added to the carrier material. PBS is commercially available. Subsequently the protein to be immobilized is added in solution or suspension and incubated for a few hours, for example overnight, preferably while gently shaking. The product is then washed with a suitable buffer, e.g. PBS, subsequently with 10% by volume of ethanolamine in PBS buffer solution with a pH value of 8.0., saturated and held at room temperature for a period of time, for example up to about 4 hours, while gently shaking. Finally, the gel is washed with PBS in order to completely remove the ethanolamine.

The immobilized protein can be stored at low temperature, i.e., about 4° C. in PBS preferably with a suitable preservative, for example THIMEROSAL, at about 0.02% by weight.

The modified membrane material, described above, is bonded to a protein in basically an analogous manner. Thus, the membrane material is treated with a standard phosphate buffer (PBS) and the protein is added. Preferably one incubates for several hours, for example, overnight at room temperature and with gentle shaking. Then, the product is washed with PBS and saturated with a 10% ethanolamine solution (pH 8.0). After a period of time, for example about four hours with gentle shaking, the protein-bonded membrane material is washed with PBS and is available for further application.

The advantageous effects of the modified, solid carriers of the present invention are derived from the fact that, instead of the one functional group on a given carrier material for example an epoxy group of the carrier materials that is capable of covalent bonding; there are four reactive chlorine atoms available (although not all chlorine atoms always participate in the bonding) for bonding. The bonding capacity for proteins is drastically increased, as is clear from the comparison made below (Table 1).

There are many carrier materials which contain XM groups or can be converted into such groups and these are available as the starting materials for this invention.

Other features of the invention will become apparent in the course of the following descriptions of exemplary embodiments which are given for illustration of the invention and are not intended to be limiting thereof.

EXAMPLES

Example 1. A Carrier Material Which Contains Epoxy Groups

A1. Reaction of carrier material EUPERGIT C with ammonia.

To one gram of the carrier material EUPERGIT C, was added 4 ml of 1.0M NH$_4$OH. This mixture was incubated for 72 hours at room temperature with gentle shaking. The gel produced was then washed with distilled water and saturated with 5% mercaptoethanol at a pH of 8.0. The saturated gel was incubated overnight at room temperature with gentle shaking. The gel was then washed with distilled water and dried with acetone over a glass frit. The dry gel was further dried overnight in a vacuum-drying oven at approximately 40° C. to obtain an amino group-containing carrier material.

B1. Conversion of the amino group-containing material of Example A1 to a carrier material having groups of formula I.

To one gram of the amino group-containing carrier material of Example A1 was added 10 ml of 0.1M sodium carbonate buffer having a pH of 10.8. Trichloro-triazine (0.15 g) was dissolved in 2 ml of acetone and added dropwise to the amino group-containing EUPERGIT carrier. This mixture was then incubated for 10 minutes at room temperature with gentle shaking after which the pH was readjusted to pH 10.8 with sodium carbonate buffer. The carrier material was then washed with 50% acetone in a glass column and vacuum dried to obtain a carrier having groups of formula IV.

10 ml of 25% ammonia was added to the dried carrier and this mixture was incubated for 30 minutes at 60° C. with gentle shaking. After washing with water and then acetone, the gel which was obtained was vacuum dried. To the dried gel was added 10 ml of 0.1M sodium carbonate buffer (pH 10.8) and 0.3 g of trichloro-triazine dissolved in acetone was added dropwise. This mixture was then incubated for 8 minutes at room temperature with gentle shaking. The pH was readjusted with sodium carbonate buffer to a pH of 10.8. The gel was then washed with 50% acetone, vacuum dried and finally freeze dried to obtain a carrier material having functional groups of formula I.

C1. Coupling of a protein to the carrier material 0.25 g of the carrier material from Example B1 (1 ml of gel) was mixed with 500 microliters of PBS. To this mixture was added 1 ml of protein A (5 mg/ml) and the mixture was incubated overnight at room temperature with gentle shaking. The gel obtained was washed with PBS, saturated with a 10% ethanolamine/PBS solution (pH 8.0) and shaken gently for four hours at room temperature. The gel obtained was then washed with PBS.

Example 2. Use of a Membrane as the Carrier Material

B2. Reaction of an amino group-containing membrane material with trichloro-triazine.

0.15 g of trichloro-triazine dissolved in 2 ml of nitromethane was added dropwise to a membrane material (BIODYNE A) having dimensions of 2 cm². After incubating 10 minutes at room temperature with gentle shaking, the membrane was washed with nitromethane and air dried to obtain a membrane material having groups of formula IV. To this membrane material was then added 10 ml of 25% ammonia. This mixture was incubated for 30 minutes at 60° C. with gentle shaking and then washed with water and dried. Trichloro-triazine dissolved in 4 ml of nitromethane was then added dropwise to the dried membrane material and this mixture was incubated for 8 minutes at room temperature with gentle shaking. After washing the membrane obtained with nitromethane, the membrane was air dried and subsequently freeze dried to obtain a membrane containing groups having formula I.

C2. Coupling of protein A to the membrane material of example B1.

A 2 cm² portion of the membrane of example B2 was used in this example. To the membrane material was added 500 microliters of PBS followed by addition of 1 ml of protein A (150 μg/ml). The mixture was incubated overnight at room temperature with gentle shaking. After washing with PBS, the membrane was saturated with a 10% solution of ethanolamine in PBS (pH 8.0) and shaken gently for four hours at room temperature. A suitable protein-bonded membrane material was obtained after washing with PBS.

The advantages, which can be achieved by coupling a biomolecule (protein) to the carriers of the present invention are shown with the aid of Tables 1 and 2.

TABLE 1

Bonding capacity for immunoglobulin G (IgG)

| Coupling Method | Protein A immobilized per g of gel (moist) (mg) | Bonded IgG per g of gel (moist) (mg) |
| --- | --- | --- |
| ®EUPERGIT C unmodified (prior art) | 10 | 7 |
| matrix containing groups of formula (IV) | 5 | 12 |
| matrix containing groups of formula (I) (Example B1) | 5 | 20 |

TABLE 2

Bonding capacity for immunoglobulin G (IgG)

| Coupling Method | Protein A immobilized per 2 cm² membrane | Bonded IgG per 2 of cm² membrane |
| --- | --- | --- |
| membrane material containing epoxy groups/direct bonding | 150 μg | 100 μg |
| matrix containing groups of formula (IV) | 150 μg | 375 μg |
| matrix containing groups of formula (I) (Example B2) | 150 μg | 600 μg |

Obviously, numerous modifications and variations of the present invention are possible in light of the above teachings. It is therefore to be understood that within the scope of the appended claims, the invention may be practiced otherwise than as specifically described herein.

What is new and desired to be secured by Letters Patent of the United States is:

1. A modified solid carrier for covalent immobilization of proteins, comprising a solid matrix material having covalently bonded thereto functional groups of formula I

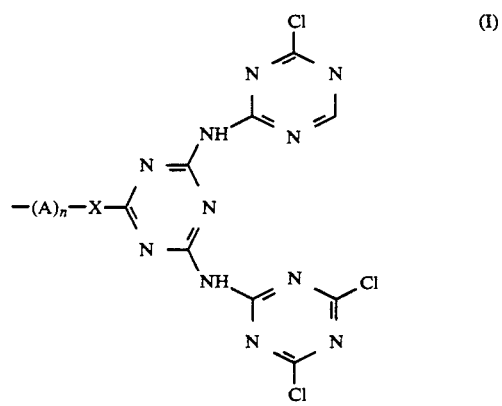

wherein A is a spacer group, X is O, S or NH and n=0 or 1.

2. The modified solid carrier of claim 1, wherein said solid matrix material is selected from the group consisting of cross-linked copolymers of methacrylamide and acrylamide, and polysaccharides.

3. The modified solid carrier of claim 2, wherein said polysaccharide is cellulose, agarose or sepharose.

4. The modified solid carrier of claim 2, wherein said cross-linked copolymer is cross-linked with N,N-methylene-bis-methacrylamide cross-linking monomer units.

5. The modified solid carrier of claim 1, wherein A is $$-(CH_2-CH-CH_2)-$$
$$\phantom{-(CH_2-}|$$
$$\phantom{-(CH_2-}OH$$

and X is NH.

6. The modified solid carrier of claim 1, wherein said matrix material is a membrane.

7. The modified solid carrier of claim 1, wherein said matrix material is a macroporous bead.

8. The modified solid carrier of claim 7, wherein said macroporous bead has a diameter of 5–1,000 microns.

9. The modified solid carrier of claim 1, wherein said matrix material is a solid bead having essentially no pore content.

10. The modified solid carrier of claim 1, having covalently bonded to said functional groups a biocatalyst.

11. The modified solid carrier of claim 10, wherein said biocatalyst is a microorganism.

12. The modified solid carrier of claim 10, wherein said biocatalyst is an enzyme or antibody.

13. The modified solid carrier of claim 10, wherein said biocatalyst is a cell.

14. The modified solid carrier of claim 10, wherein said biocatalyst is a cell organelle.

15. The modified solid carrier of claim 10, wherein said biocatalyst is a virus.

16. The modified solid carrier of claim 10, wherein said biocatalyst is a protein.

17. A method of immobilizing a biomolecule on a solid carrier, comprising covalently bonding said biomolecule to functional groups covalently bonded to a solid carrier, said functional groups having formula I

[Structure of Formula (I): $-(A)_n-X-$ linked to a tris-triazinyl system with three chloro-triazine rings]

wherein A is a spacer group, X is O, S or NH and n=0 or 1.

18. A process for preparing a modified solid carrier for covalent immobilization of proteins, comprising a solid matrix material having covalently bonded thereto functional groups of formula I

[Structure of Formula (I): $-(A)_n-X-$ linked to a tris-triazinyl system with three chloro-triazine rings]

wherein A is a spacer group, X is O, S or NH and n=0 or 1, comprising the steps of:

reacting ammonia with functional groups covalently bonded to a solid matrix, said functional groups having the formula II $$-CH_2-CH-CH_2 \qquad \text{(II)}$$
$$\phantom{-CH_2-}\underset{O}{\diagdown\diagup}$$

to form a matrix comprising α-hydroxy-β-amino groups of formula III;

$$\phantom{-CH_2-}\overset{OH}{\underset{|}{\phantom{C}}} \qquad \text{(III)}$$
$$-CH_2-CH-CH_2NH_2$$

reacting the α-hydroxy-β-amino groups with 2,4,6-trichloro-s-triazine to form a matrix having N-triazinyl groups of formula IV:

$$-CH_3-\overset{OH}{\underset{|}{CH}}-CH_2-NH-\overset{N=\phantom{x}}{\underset{N-\phantom{x}}{\bigg\langle}}\overset{Cl}{\underset{Cl}{\phantom{x}}} \qquad \text{(IV)}$$

reacting said N-triazinyl group-containing matrix with ammonia to form a carrier having groups of formula V; and $$-CH_3-\overset{OH}{\underset{|}{CH}}-CH_2-NH-\overset{N=\phantom{x}}{\underset{N-\phantom{x}}{\bigg\langle}}\overset{NH_2}{\underset{NH_2}{\phantom{x}}} \qquad \text{(V)}$$

reacting said matrix having groups of formula V with two equivalents of 2,4,6-trichloro-s-triazine to obtain a carrier having groups of formula I.

* * * * *

UNITED STATES PATENT AND TRADEMARK OFFICE
CERTIFICATE OF CORRECTION

PATENT NO. : 5,266,471

DATED : November 30, 1993

INVENTOR(S) : Stefan Schmitt

It is certified that error appears in the above-indentified patent and that said Letters Patent is hereby corrected as shown below:

In the Abstract, delete Formula (I) in its entirety and replace with --

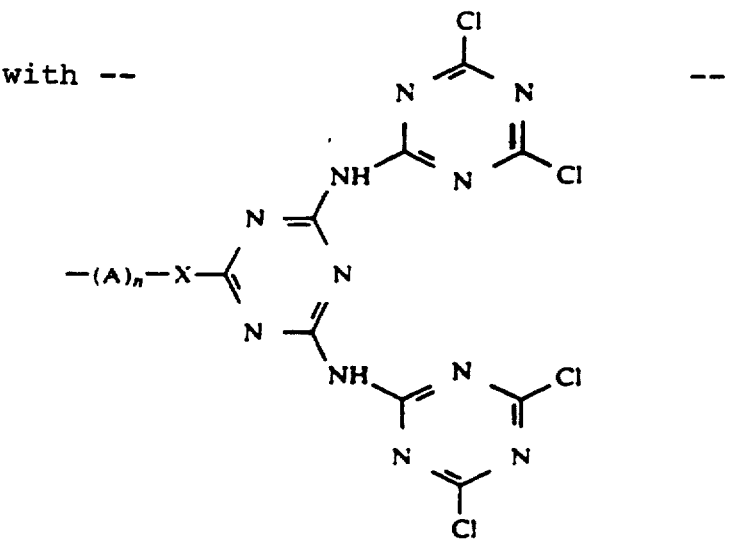

--

UNITED STATES PATENT AND TRADEMARK OFFICE
CERTIFICATE OF CORRECTION

PATENT NO. : 5,266,471
DATED : November 30, 1993
INVENTOR(S) : Stefan Schmitt

It is certified that error appears in the above-indentified patent and that said Letters Patent is hereby corrected as shown below:

Column 2, lines 30-44, delete Formula (I) in its entirety and replace with -- 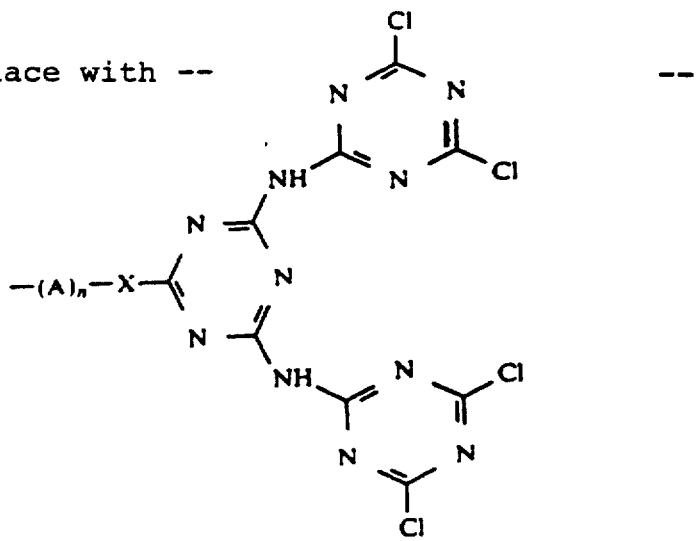 --

Column 3, lines 54 and 55, delete "formula II" and insert --formula III--;
    line 56, delete "NCl" and insert --HCL--;
    line 66, delete "stop" and insert --step--.

Column 5, lines 30-31, delete "U.S. Pat. No. 4,829,101)" and insert --(U.S. Pat. No. 4,829,101)--.

Column 6, line 55, delete "take".

Column 7, line 10, after "slightly", delete "and"

UNITED STATES PATENT AND TRADEMARK OFFICE
CERTIFICATE OF CORRECTION

PATENT NO. : 5,266,471

DATED : November 30, 1993

INVENTOR(S) : Stefan Schmitt

Page 3 of 5

It is certified that error appears in the above-indentified patent and that said Letters Patent is hereby corrected as shown below:

Column 10, line 44, Claim 1, delete "formula (I)" in its entirety and replace with --

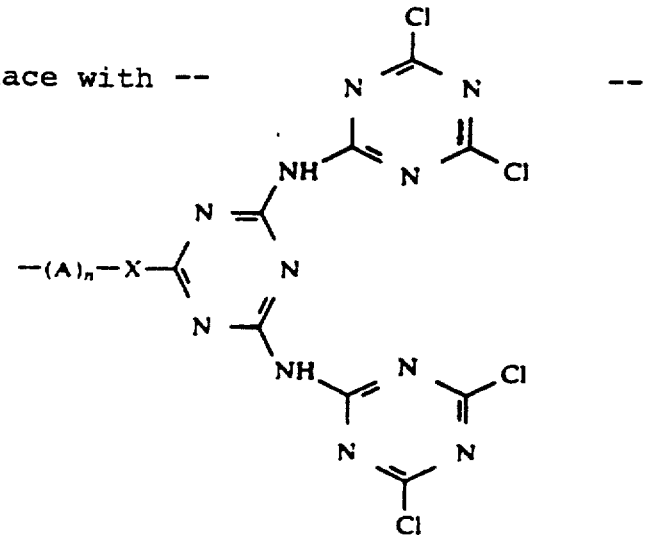

--

UNITED STATES PATENT AND TRADEMARK OFFICE
CERTIFICATE OF CORRECTION

PATENT NO. : 5,266, 471
DATED : November 30, 1993
INVENTOR(S) : Stefan Schmitt

Page 4 of 5

It is certified that error appears in the above-indentified patent and that said Letters Patent is hereby corrected as shown below:

Column 11, lines 45-60, Claim 17, delete "formula (I)" in its entirety and replace with --

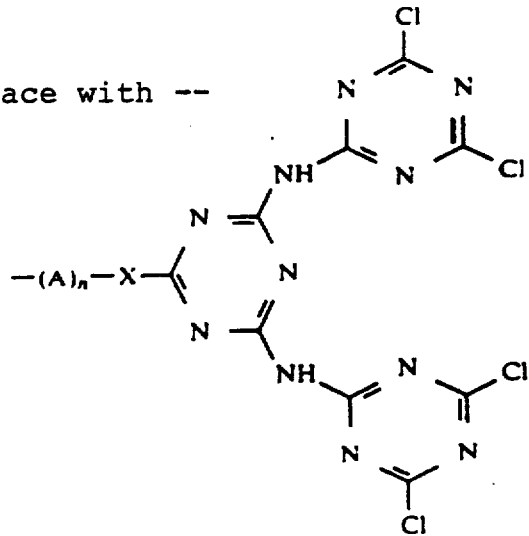

UNITED STATES PATENT AND TRADEMARK OFFICE
CERTIFICATE OF CORRECTION

PATENT NO. : 5,266,471
DATED : November 30, 1993
INVENTOR(S) : Stefan Schmitt

It is certified that error appears in the above-indentified patent and that said Letters Patent is hereby corrected as shown below:

Column 12, lines 5-19, delete "formula (I)" in its entirety and replace with --

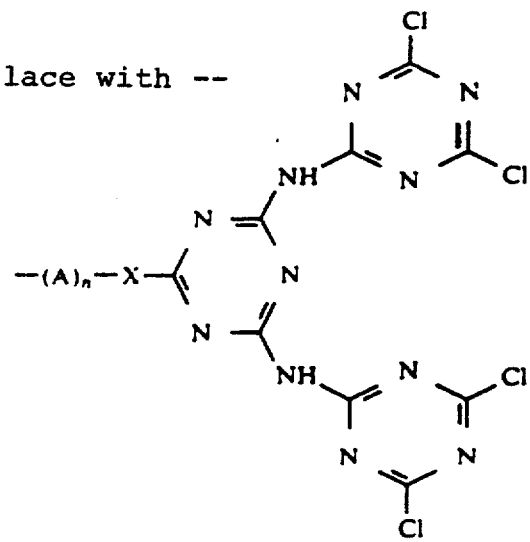

--

Signed and Sealed this

Twenty-seventh Day of September, 1994

Attest:

BRUCE LEHMAN

Attesting Officer

Commissioner of Patents and Trademarks